United States Patent
Ryu et al.

(10) Patent No.: US 7,026,529 B2
(45) Date of Patent: Apr. 11, 2006

(54) **METHODS FOR *AGROBACTERIUM*-MEDIATED TRANSFORMATION OF DANDELION**

(75) Inventors: Stephen Beungtae Ryu, Kwangju (KR); Hyo-Yeon Lee, Cheju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 436 days.

(21) Appl. No.: 10/601,883

(22) Filed: Jun. 24, 2003

(65) Prior Publication Data

US 2005/0022267 A1    Jan. 27, 2005

(51) Int. Cl.
*C12N 15/82*    (2006.01)

(52) U.S. Cl. ...................................... 800/294

(58) Field of Classification Search ................. 800/294
See application file for complete search history.

(56) References Cited

OTHER PUBLICATIONS

Song et al. 1991. Acta Horticulturae 289: 261-262.*
Michalska et al, Letter . . . Planta Med 2003; 69, pp. 181-183, Sesquiterpene Lactones from *Taraxacum obovatum*.
Yun et al, Biosci. Biotechnol. Biochem. 66(9), 2002, pp. 1859-1864, Anticoagulant from *Taraxacum platycarpum*.
Zielinska et al, PHYTOCHEMISTRY 54 (2000), pp. 791-794, Sesquiterpenoids from roots of *Taraxacum laevigatum* and . . . .
Ho et al, Letters . . . Planta Med 64 (1998), pp. 577-578, Desacetylmatricarin, an Anti-Allergic Component from . . . .
Booth et al, New Phytol. (1974) 73, pp. 453-460, Regeneration in Root Cuttings in *Taraxacum officinale*.
Bowes, PROTOPLASMA 71, (1970), pp. 197-202, Preliminary Observations on Organogenesis in *Taraxacum officinale* Tissue . . . .

* cited by examiner

*Primary Examiner*—David H. Kruse
*Assistant Examiner*—Keith O. Robinson
(74) *Attorney, Agent, or Firm*—Jacobson Holman PLLC

(57) ABSTRACT

Methods for *Agrobacterium*-mediated transformation and regeneration of dandelion plants are disclosed.

14 Claims, 2 Drawing Sheets

METHODS FOR *AGROBACTERIUM*-MEDIATED TRANSFORMATION OF DANDELION

FIELD OF THE INVENTION

The invention relates to methods of genetically transforming plants and more specifically to a method for *Agrobacterium*-mediated transformation of dandelion

BACKGROUND OF THE INVENTION

Plants of the genus *Taraxacum* have been used in herbal medicine owing to their choleretic, diuretic and anti-carcinogenic activities (Ho et al. 1998, Takasaki et al 1999, Ahmad et al. 2000, Yun et al 2002). From the roots of the plant, several medicinal compounds including the guaianolide desacetylmatricarin, and the germacranolides taraxinic acid β-glucopyranosyl ester, sonchuside A were isolated (Ho et al. 1998; Zielinska and Kisiel 2000). Recently two new guaianolide glucosides, desacetylmatricarin 8-O-β-glucopyranoside and 11β-hydroxyleukodin 11-O-β-glucopyranoside were also isolated (Michalska and Kisiel 2003). The triterpenoids taraxasterol and taraxerol isolated from dandelion roots exhibited potent anti-tumor-promoting activity (Takasaki et al 1999).

Dandelion also produces useful secondary metabolites such as natural rubber in latex. Metabolic engineering of secondary metabolite biosynthesis pathways has become an area of great biotechnological interest during the last decade. The development of methods for the introduction of foreign genes into plants has led to significant advances in the field of metabolic engineering of plant secondary compounds and had a profound impact on the areas of medicine and agriculture.

Both et al. (1974, New Phytol. 73:453–460) regenerated new shoots from root segments of *Taraxacum officinale*.

Bowes et al. (1970, Protoplasma 71:197–202) observed organogenesis in *Taraxacum officinale* tissue cultures.

Yeo et al. (2001, Korean J. Plant Biotechnology 16:480–485) describe the transformation of dandelion (*Taraxacum mongolicum*) using *Agrobacterium tumefaciens* strain LBA4404 harboring a binary vector pBI121, where transformation efficiency was 2 to 3%.

Lee et al. (2002, Korean J. Plant Biotechnology 29:111–115) investigated effects of auxin and cytokinin on adventitious shoot formation from seedling explants of *Taraxacum platycarpum*.

To promote the engineering of desirable traits into the plant, there exists a need for efficient dandelion transformation and regeneration methods.

SUMMARY OF THE INVENTION

The present invention relates to methods of preparing transgenic dandelion plants. In a preferred embodiment, the invention describes a method for the preparation of transgenic dandelion explants comprising contacting dandelion explants with *Agrobacterium tumefaciens* in a co-cultivation medium containing acetosyringone, glucose and betaine.

The *Agrobacterium tumefaciens* may generally contain a nucleic acid sequence endogenous to *Agrobacterium tumefaciens*, a nucleic acid sequence endogenous to dandelion, or a nucleic acid sequence from another organism. Alternatively, the *Agrobacterium tumefaciens* contains a nucleic acid sequence exogenous to dandelion, exogenous to *Agrobacterium tumefaciens*, or exogenous to both dandelion and *Agrobacterium tumefaciens*. The nucleic acid sequence may comprise a selectable marker. The selectable marker may generally be any selectable marker suitable for use in *Agrobacterium tumefaciens* or dandelion, and preferably is NPT II, HPT, or EPSPS.

The co-cultivation medium preferably contains acetosyringone. The acetosyringone concentration may generally be about 0.01 mM to about 1.0 mM, preferably about 0.05 mM to about 0.5 mM, and more preferably about 0.1 mM to about 0.2 mM. The co-cultivation medium preferably contains glucose and betaine. The concentration of glucose may generally be about 1% (w/v) to about 3% (w/v). The concentration of betaine may generally be about 50 mg/l to about 100 mg/l.

The method may further comprise an incubation step for incubating the transformed dandelion explants in shoot induction media before hygromycin selection. The incubation period may be about 2 to about 12 days, preferably about 5 to about 9 days, and more preferably is about 7 days.

The shoot induction medium preferably contains maltose. The maltose concentration may generally be about 0.1% (w/v) to about 5% (w/v), and preferably about 0.5% (w/v) to about 3% (w/v). The explants may generally be prepared from any dandelion tissue, and preferably is prepared from either micropropagated dandelion cultures or pot-grown dandelion leaves.

In an alternative embodiment, the invention describes a method for the preparation of transgenic dandelion shoots comprising culturing transformed dandelion explants in selection medium. The selection medium may contain an auxin, a cytokinin, an antibiotic, or a plant selection agent.

The selection medium preferably contains maltose. The maltose concentration may generally be about 0.1% (w/v) to about 5% (w/v), and preferably about 1% (w/v) to about 3% (w/v).

The invention further encompasses a method for the preparation of transgenic dandelion plants comprising culturing transformed dandelion shoots in rooting medium.

The invention further encompasses dandelion plants produced by any of the above described methods.

The features and details of the invention will be more fully appreciated in light of the following detailed description of the invention.

Definitions

The following definitions are provided as an aid to understanding the detailed description of the present invention.

"Adaxial" refers to the upper surface of an expanded leaf or petal.

"Auxin" refers to a class of plant hormones that promotes growth in plant cells and tissues by elongation rather than by the multiplication of cells. The auxin induces cell elongation by causing the cell wall to soften at the "growing" end of the cell.

"Callus" refers to a proliferating mass of plant cells or tissue in vitro.

"Cytokinin" refers to a class of plant hormones whose principle functions are the induction of cell division (cytokinesis) and the regulation of tissue differentiation.

"Explant" refers to a piece of tissue or an organ removed from a plant to start a plant cell culture.

The phrase "low light conditions" refers to a light intensity of about 0 $\mu$Einsteins m$^{-2}$ sec$^{-1}$ to about 40 $\mu$Einsteins m$^{-2}$ sec$^{-1}$.

"Nucleic acid" refers to deoxyribonucleic acid (DNA) and ribonucleic acid (RNA).

"Transformation" refers to the introduction of nucleic acid into a recipient host or hosts.

"Host" or "hosts" refers to entire plants, plantlets, or plant parts such as plant cells, protoplasts, calli, roots, tubers, propagules, seeds, seedlings, pollen, and plant tissues.

"Transgenic" refers to organisms into which new nucleic acid sequences are added.

BRIEF DESCRIPTION OF THE DRAWINGS

FIG. 2A, Two wild-type and five independent transgenic $R_1$ dandelion plants. RNA obtained from. $R_1$ generation-transformed plants exhibited a 986 bp band, but except transgenic plant number 2, implying the presence of false-positive transgenic plants among hygromycin-resistant plants. FIG. 2B, Two wild-type and five independent transgenic $R_2$ dandelion plants. Total RNA was isolated from wild-type and transgenic plants of dandelion, reverse-transcribed with gene-specific primers and used as templates for PCR, resulting in the amplification of a 986 bp GUS cDNA fragment and 303 bp 18S rRNA fragment. RT-PCR analysis revealed similar levels of GUS expression in five independent $R_2$ transgenic lines, suggesting stabilized gene expression.

DETAILED DESCRIPTION OF THE INVENTION

Figure 1:
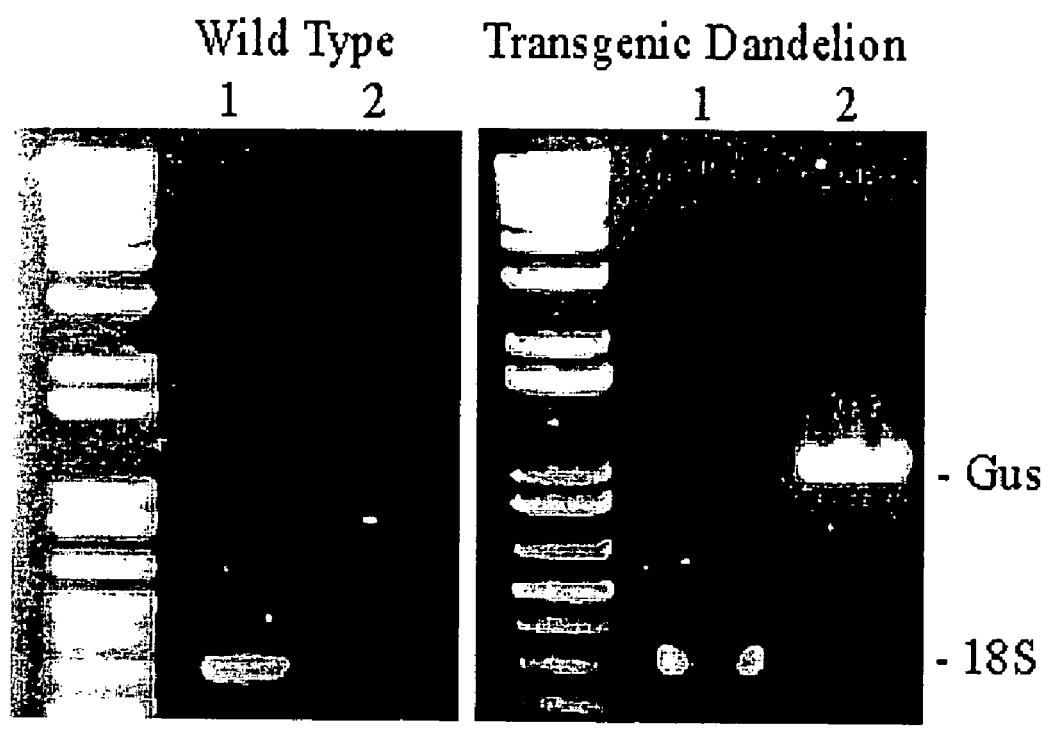
FIG. 1 PCR analysis of genomic dandelion DNA using primers specific for the GUS gene and 18S as a control. 18S (Lane 1) and GUS (Lane 2) PCR products of wild-type and hygromycin-resistant dandelions, respectively. A PCR product was observed with the 18S control, but not with GUS primers in wild type plants. PCR products with both GUS and 18S primers were observed in hygromycin-resistant shoots, indicating that the GUS gene is integrated into the dandelion genome.

The present invention involves methods for the transformation and preparation of transgenic dandelion plants.

An appropriate DNA sequence is selected for introduction into the dandelion plant cells. As useful gene for introduction into dandelion plant cells, the kinds of genes do not have to be limited. However, as a preferred example, rubber-biosynthesis related genes (rubber polymerase, cis-prenyl-transferase, isopentenyl pyrophosphate synthase); medical proteins (albumin) can be exemplified.

The sequence typically contains a gene of interest, a promoter functional to direct transcription of the gene, and a selectable marker to facilitate identification of the transformed plant cells. Examples of selectable markers include, but are not limited to, the neomycin phosphotransferase, hygromycin phosphotransferase, and EPSPS genes.

Expression of the selectable marker confers resistance to a selective agent. Growth of plant cells on medium containing the selective agent allows phenotypic differentiation of the transgenic and non-transgenic plant cells. Cells lacking the selectable marker are unable to grow in the presence of the selective agent.

Explants are obtained from either dandelion cultures grown in microproagation media or from pot-grown dandelion leaves. The explants are placed onto preculture plates and placed under mixed white and red lights (1:1) prior to transformation.

Co-culturing of leaf explants and a liquid culture of *Agrobacterium tumefaciens* bacteria harboring the DNA plasmid is performed for approximately 15–30 minutes. The bacterial culture is removed, and the explants are briefly dried and stored in the dark or under low light conditions at approximately 22.degree. C. for about two days to continue co-culturing with the *Agrobacterium tumefaciens*.

Explants are moved to shoot induction medium for about seven days at approximately 22.degree. C. The samples are kept under mixed white and red lights (1:1) during the incubation in shoot induction medium.

The samples are transferred onto selection medium containing about 1% maltose and appropriate selective agents, and cultured for about three weeks. Subcultures are performed approximately every three weeks. Transformed explants produce green shoots and green callus. Explants containing green shoots and callus are selected for further processing.

Shoots are rooted on rooting medium for about three to four weeks. Shoots are potted in soil to grow into dandelion plants.

EXAMPLES

Experimental Protocols

The following protocols are included to specify conditions, components, and methods involved in the preparation of transgenic dandelion plants. One skilled in the art will recognize that changes to the compositions, concentrations, times, and steps may be made without deviating from the scope and spirit of the invention. Where alternative compositions or methods are available, they are indicated by different letters, e.g. media A, media B, method A, method B.

Dandelion Transformation Protocol

Stock Plant Preparation A

Dandelion seeds are surface-sterilized in approximately 70% (volume/volume, v/v) ethanol for 30 sec in the bottle. The ethanol is removed and the seeds are soaked in approximately 1% (v/v) bleach with gentle agitation for about 15 minutes. The bleach is poured off and the leaves are rinsed thoroughly about 3–4 times with sterilized distilled water. Seeds are germinated and in vitro cultured in the sterile bottles containing seedling medium (Table 1). Over one month-old seedlings are used as stock plants for leaf and root explants.

TABLE 1

| Seedling medium | |
|---|---|
| Component | Concentration |
| MS salts/vitamins (DUCHEFA M 0222) | 4.4 g/L |
| sucrose | 30 g/L |
| Phytagel | 0.2% (w/v) |

Stock Plant Preparation B

Stock plants are also grown in pots containing soil mixture (peat:vermiculite:perite=1:1:1) in the greenhouse. The leaves or roots are surface sterilized by rinsing in water in a sterile bottle. The leaves or roots are then briefly immersed in approximately 70% (v/v) ethanol for 30 sec in the bottle. The ethanol is removed and the leaves are soaked in approximately 1% (v/v) bleach with gentle agitation for about 15 minutes. The bleach is poured off and the leaves are rinsed thoroughly about 3–4 times with sterilized distilled water.

Explant Preparation/Pre-Incubation

The leaves and roots of stock plants are placed in a petri plate with droplets of sterile water. Explants of leaves (ca. 0.5 cm in diameter) and of roots (ca. 0.5 cm in length) were excised from dandelion plants. Approximately 15 to 20 explants per plate are positioned with the adaxial surface down onto pre-incubation medium (Table 2). The plates are incubated under mixed white and red lights for about 6 days at about 22.degree. C.

TABLE 2

Pre-incubation medium

| Component | Concentration |
| --- | --- |
| MS salts/vitamins (DUCHEFA M 0222) | 4.4 g/L |
| α-naphthalene acetic acid | 0.1 mg/L |
| 6-benzyladenine | 2.0 mg/L |
| acetosyringone | 0.1 mM |
| betaine | 50 mg/L |
| glucose | 20 g/L |
| sucrose | 30 g/L |
| Phytagel | 0.2% (w/v) |
| pH adjusted to 5.2 | |

*Agrobacterium* Preparation

*Agrobacterium* is cultured overnight from a frozen stock in 50 ml media containing rifampicin, and kanamycin (denoted LB-KR, Table 3) until the optical density at 660 nanometers reaches to about 0.8. The overnight culture is centrifuged, and the pellet is suspended in 50 ml induction solution (Table 4). The suspended culture is incubated for 1 h at 28° C. This *Agrobacterium* culture is used as the inoculum.

TABLE 3

LB-KR medium

| Component | Concentration |
| --- | --- |
| Sodium chloride | 10 g/L |
| Tryptone | 10 g/L |
| Yeast extract | 5 g/L |
| Difco bacto agar | 15 g/L |

TABLE 4

Induction solution

| Component | Concentration |
| --- | --- |
| MS salts/vitamins (DUCHEFA M 0222) | 2.2 g/L |
| MES | 0.5 g/L |
| acetosyringone | 0.1 mM |
| betaine | 50 mg/L |
| glucose | 20 g/L |
| sucrose | 30 g/L |
| pH adjusted to 5.2 | |

Inoculation/Co-Cultivation

After the six-day pre-incubation period, the leaf or root explants are then incubated in the tube with the *Agrobacterium* suspension for about 15–30 minutes. Enough *Agrobacterium* suspension is added to just cover explants. The tissue is blotted on a sterile WHATMAN filter paper (WHATMAN is a registered trademark of Whatman International, Ltd., Hillsboro, Oreg.) and placed on co-cultivation plates containing pre-incubation medium (Table 2). The plates are then incubated in the dark for about 2 days at approximately 22.degree. C.

Shoot Induction before Hygromycin Selection

After the approximately 2 day co-culture period, the explants are washed with washing solution (Table 5), briefly dried, and transferred to shoot induction medium (Table 6). The explants are incubated on these plates for 7 days at approximately 22–25.degree. C.

TABLE 5

Washing solution

| Component | Concentration |
| --- | --- |
| MS salts/vitamins (DUCHEFA M 0222) | 2.2 g/L |
| Ascorbic acid | 0.25 g/L |
| sucrose | 15 g/L |
| cefotaxim | 250 mg/L |
| pH adjusted to 5.8 | |

TABLE 6

Shoot induction medium

| Component | Concentration |
| --- | --- |
| MS salts/vitamins (DUCHEFA M 0222) | 4.4 g/L |
| α-naphthalene acetic acid | 0.1 mg/L |
| 6-benzyladenine | 2.0 mg/L |
| maltose | 10 g/L |
| sucrose | 30 g/L |
| cefotaxim | 250 mg/L |
| Phytagel | 0.2% (w/v) |
| pH adjusted to 5.8 | |

Selection Method

After 7 days, the leaves are transferred to selection medium (Table 7). The explants are cultured at about 22.degree. C. and in mixed white and red lights (1:1). The explants are subcultured to fresh medium every two weeks. Shoots are rooted on root induction medium (Table 8). The rooting step may take 4–5 weeks. Regenerated plants are potted into 3-inch pots containing a mixture of peat, vermiculite and perite (1:1:1). The containers are covered with plastic wrap for 3 days. Subsequently, several holes were made on the cover of plastic wrap to allow for airflow for 3 more days. The wrap is partially opened after 6 days and plants stay under half-opened cover for an additional 10 to 15 days. Plants are then transplanted into 6-inch pots containing a mixture of peat, vermiculite and perite (1:1:1). Greenhouse temperatures range from about 20–25.degree. C.

TABLE 7

Selection medium

| Component | Concentration |
| --- | --- |
| MS salts/vitamins (DUCHEFA M 0222) | 4.4 g/L |
| α-naphthalene acetic acid | 0.1 mg/L |

TABLE 7-continued

Selection medium

| Component | Concentration |
|---|---|
| 6-benzyladenine | 2.0 mg/L |
| maltose | 10 g/L |
| sucrose | 30 g/L |
| cefotaxim | 250 mg/L |
| hygromycin | 25 mg/L |
| Phytagel | 0.2% (w/v) |
| pH adjusted to 5.8 | |

TABLE 8

Root induction medium

| Component | Concentration |
|---|---|
| MS salts/vitamins (DUCHEFA M 0222) | 4.4 g/L |
| α-naphthalene acetic acid | 0.1 mg/L |
| 6-benzyladenine | 2.0 mg/L |
| maltose | 10 g/L |
| sucrose | 30 g/L |
| cefotaxim | 250 mg/L |
| Phytagel | 0.2% (w/v) |
| pH adjusted to 5.8 | |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Effect of Phyto-hormones on Dandelion Regeneration

Table 9 displays percentage of leaf explants displaying adventitious shoot formation after four weeks of culture on seedling media (Table 1) containing 6-benzyladenine or kinetin in combination with α-naphthalene acetic acid at different concentrations. Parentheses indicate the number of regenerated shoots per explant. Combinations of 1 or 2 mg/l 6-benzyladenine and 0.1 mg/l α-naphthalene acetic acid were the most suitable for shoot regeneration of dandelion, based on the percentage of explants displaying shoot formation, the number of regenerated shoots per leaf explant, and regenerated leaf morphology (Table 9). In contrast, a combination of either 0.05 mg/l α-naphthalene acetic acid and 1.0 mg/l kinetin or 0.1 mg/l α-naphthalene acetic acid and 2.0 mg/l kinetin was also suitable for dandelion shoot regeneration (Table 9).

TABLE 9

| α-Naphthalene acetic acid (mg/L) | 6-Benzyladenine (mg/L) | | | | | Kinetin (mg/L) | | | | |
|---|---|---|---|---|---|---|---|---|---|---|
| | 0 | 0.25 | 0.5 | 1.0 | 2.0 | 0 | 0.5 | 1.0 | 2.0 | 3.0 |
| 0 | 10.0 | 60.0 | 75.0 | 85.0 | 99.9 | 10.0 | 99.9 | 99.9 | 95.0 | 99.9 |
| | (1.0) | (21.2) | (17.4) | (17.4) | (16.0) | (1.0) | (24.8) | (22.7) | (21.9) | (14.7) |
| 0.1 | 0.0 | 63.0 | 99.9 | 99.9 | 99.9 | 0.0 | 96.7 | 99.9 | 99.9 | 99.9 |
| | (0.0) | (16.3) | (23.8) | (25.1) | (17.4) | (0.0) | (19.8) | (23.4) | (23.6) | (19.3) |
| 0.5 | 20.0 | 78.0 | 99.9 | 99.9 | 99.9 | 0.0 | 99.9 | 99.9 | 99.9 | 99.9 |
| | (2.0) | (12.0) | (23.7) | (20.4) | (20.7) | (0.0) | (16.9) | (16.8) | (20.3) | (25.5) |
| 1.0 | 0.0 | 97.0 | 88.0 | 83.0 | 99.9 | 5.0 | 99.9 | 99.9 | 95.5 | 99.9 |
| | (0.0) | (24.5) | (21.7) | (13.1) | (8.5) | (0.0) | (8.1) | (6.7) | (13.4) | (8.9) |
| 2.0 | 0.0 | 90.0 | 40.0 | 99.9 | 99.9 | 0.0 | 99.9 | 99.9 | 96.2 | 99.9 |
| | (0.0) | (3.6) | (3.2) | (5.9) | (5.4) | (0.0) | (5.8) | (9.8) | (7.3) | (8.1) |

EXAMPLE 2

Effect of Maltose on Shoot Regeneration

Leaf explants derived from dandelion plants were cultured in shoot induction media containing no maltose (w/v) or 1% maltose (w/v) to compare the efficacy of maltose on shoot production. Table 10 demonstrates that maltose improves shoot production in comparison to no maltose.

TABLE 10

| Maltose (%) | # of Shoots per Explants |
|---|---|
| 0 | 16 |
| 1 | 25 |

EXAMPLE 3

Effect of Explant Type on Regeneration Response

Leaf or root explants derived from dandelion plants were cultured in shoot induction media to evaluate the effects of explant sources on regeneration. The results indicate that roots are better source of explants than leaves (Table 11).

TABLE 11

| Explant tissue sources | |
|---|---|
| Tissue type | Days required for shooting |
| Leaves | 21 |
| Roots | 15 |

EXAMPLE 4

Effect of Incubation in Shoot Induction Medium before Selection on Transformation Efficiency Dandelion leaf explants were co-cultivated with *Agrobacterium tumefaciens* strain EHA105 carrying a binary vector, pCAMBIA1301. The explants were transferred to shoot induction medium and incubated under mixed white and red lights for 7 days at approximately 22.degree. C. Afterwards, the explants were placed in selection medium containing 50 mg/L of hygromycin and selected for hygromycin resistant calli. Table 12 shows that 7 day incubation in shoot induction medium before hygromycin selection improves the transformation efficiency by *Agrobacterium* up to 11%.

TABLE 12

| Days of Incubation | # of Explants | # of Hygromycin Resistant Calli with shoots |
| --- | --- | --- |
| 0 | 550 | 11 (2%) |
| 7 | 550 | 61 (11%) |

EXAMPLE 5

PCR of Dandelion Genomic DNA

To confirm that the GUS gene is integrated in the dandelion genome in hygromycin-resistant plants, PCR was performed using genomic DNA as a template and primers specific for both the GUS gene and the 18S ribosomal protein as a control. A PCR product was observed with the 18S control, but not with GUS primers in wild type plants (FIG. 1). PCR products with both GUS and 18S primers were observed in hygromycin-resistant shoots, indicating that the GUS gene is integrated into the dandelion genome (FIG. 1).

EXAMPLE 6

RT-PCR of Dandelion GUS Transcripts

Figure 2A:
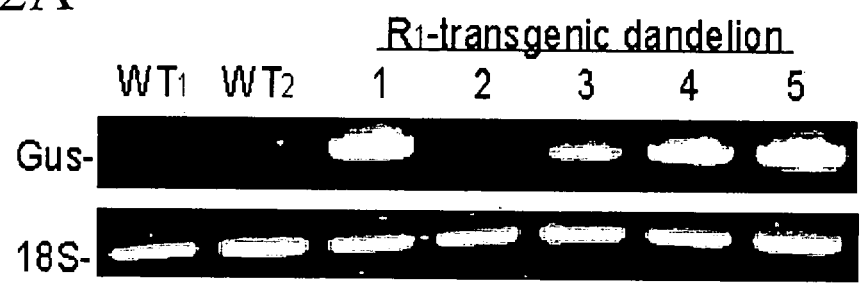
FIGS. 2A–2B show RT-PCR analysis of transgenic $R_1$ and $R_2$ dandelion plants.

To further determine whether GUS is transcribed in hygromycin-resistant plants, RT-PCR was performed using primers specific for the gene. No PCR band was observed with wild-type dandelion RNA (FIG. 2A). RNA obtained from $R_1$ generation-transformed plants exhibited a 986 bp band (FIG. 2A), but except transgenic plant number 2, implying the presence of false-positive transgenic plants among hygromycin-resistant plants. Expression of the GUS gene in transgenic plant no. 3 was low relative to that in other transgenic plants (FIG. 2A), suggesting incomplete transformation or unstable expression.

EXAMPLE 7

Progeny Data

Figure 2B:

To stabilize GUS gene expression, we generated $R_2$ transgenic plants from the root tissues of $R_1$ plants. Roots were a better source for adventitious shoot induction than leaves as previously observed by other groups. RT-PCR analysis revealed similar levels of GUS expression in five independent $R_2$ transgenic lines (FIG. 2B), suggesting stabilized gene expression. Roots were induced from $R_2$-transgenic shoots. Transgenic plants were transferred to soil pots and grown in the greenhouse.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

References

U.S. Patent Documents

| | | | |
| --- | --- | --- | --- |
| 6,274,791 * | 8/2001 | Dhir et al. | 800/278 |
| 6,483,013 * | 11/2002 | Sonville et al. | 800/278 |

Other Publications

Booth, A. et al. (1974) "Regeneration in root cutting of *Taraxacum officinale*. I. Effects of exogenous hormones on root segments and root callus cultures" New Phytol., 73:453–460.

Bowes B. G. (1970) "Preliminary observations on organogenesis in *Taraxacum officinale* tissue cultures" Protoplasma, 71:197–202.

Ho, C. et al. (1998) "Desacetylmatricarin, an anti-allergic component from *Taraxacum platycarpum*" Planta Medica, 64:577–578.

Lee, M. H. et al. (2002) "Plant regeneration and effect of auxin and cytokinin on adventitious shoot formation from seedling explant of *Taraxacum platycarpum*" Korean J. Plant Biotech., 29:111–115. [in Korean]

Michalska, K. et al. (2003) "Sesquiterpene lactones from *Taraxacum obovatum*" Planta Medica, 69:181–183.

Yeo, S. E. et al. (2001) "Transformation of *Taraxacum mongolicum* Hand. by *Agrobacterium tumefaciens*" Korean J. Biotechnol. Bioeng., 16:480–485. [in Korean]

Yun, S. I. et al. (2002) "Anticoagulant from *Taraxacum platycarpum*" Biosci. Biotechnol. Biochem., 66:1859–864.

Zielinska, K. et al. (2000) "Sesquiterpenoids from roots of *Taraxacum laevigatum* and *Taraxacum disseminatum*" Phytochemistry, 54:791–794.

What is claimed is:

1. A method of preparing transgenic shoots of a plant of the genus *Taraxacum*, the method comprising:
   (a) pre-incubating explants of said plant in a pre-incubation medium containing auxin, cytokinin, acetosyringone, glucose, sucrose, and betaine;
   (b) contacting and co-cultivating said plant explants with *Agrobacterium* cells comprising a DNA fragment of interest and an antibiotic selection marker operably linked to at least one T-DNA border in a pre-incubation medium, thereby producing transformed plant explants; and (c) culturing the transformed plant explants in a selection medium containing auxin, cytokinin, maltose, sucrose and antibiotic, thereby producing transformed plant shoots, wherein 0.05~0.5 mM of acetosyringone and 1~3% (w/v) of glucose are included in the pre-incubation media, and 0.5~3% (w/v) of maltose is included in the selection medium.

2. The method of claim 1, further comprising culturing the transformed plant shoots in root induction medium containing auxin, cytokinin, maltose, sucrose and antibiotic, thereby producing transgenic plants.

3. The method of claim 1, wherein the is plant *Taraxacum platycarpum*.

4. The method of claim 1, wherein said DNA fragment of interest is selected from the group consisting of rubber polymerase, cis-prenyltransferase, isopentenyl pyrophosphate synthase and albumin.

5. The method of claim 1, wherein said explants are from seedlings grown in vitro.

6. The method of claim 1, wherein the dandelion explants are from pot-grown plants.

7. The method of claim 1, wherein the pre-incubation period is about 0 to about 12 days.

8. The method of claim 1, wherein the pre-incubation period is about 3 to about 9 days.

9. The method of claim 1, wherein the pre-incubation period is about 6 days.

10. The method of claim 1, wherein the co-cultivation period is about 0 to about 4 days.

11. The method of claim 1, wherein the co-cultivation period is about 1 to about 3 days.

12. The method of claim 1, wherein the co-cultivation period is about 2 days.

13. The method of claim 1, further comprising incubating the transformed explants in shoot induction medium containing auxin, cytokinin, maltose, sucrose and antibiotic before hygromycin selection.

14. The method of claim 13, wherein the incubation period is about 7 days.

* * * * *